US009636466B2

(12) United States Patent
Thorley et al.

(10) Patent No.: US 9,636,466 B2
(45) Date of Patent: May 2, 2017

(54) PREFILLED RETRACTABLE SYRINGE, PLUNGER AND NEEDLE ASSEMBLY

(71) Applicant: Unitract Syringe PTY LTD., Sydney, New South Whales (AU)

(72) Inventors: Craig Stephen Thorley, Largs (AU); Joseph Hermes Kaal, Raworth (AU); Chris Rafferty, Raworth (AU); Richard Sokolov, Earlwood (AU); Ernesto Hueso, Randwick (AU); Huw Wallis, Gladesville (AU); Steve Chi Truong, Wetherill Park (AU)

(73) Assignee: Unitract Syringe Pty Ltd., Sydney, New South Wales (AU)

( * ) Notice: Subject to any disclaimer, the term of this patent is extended or adjusted under 35 U.S.C. 154(b) by 1190 days.

(21) Appl. No.: 13/688,386

(22) Filed: Nov. 29, 2012

(65) Prior Publication Data

US 2013/0338602 A1 Dec. 19, 2013

Related U.S. Application Data

(63) Continuation of application No. 12/666,448, filed as application No. PCT/AU2008/000971 on Jul. 2, 2008, now Pat. No. 8,361,035.

(Continued)

(30) Foreign Application Priority Data

Jul. 2, 2007 (AU) ................................ 2007903565

(51) Int. Cl.
*A61M 5/32* (2006.01)
*A61M 5/00* (2006.01)
(Continued)

(52) U.S. Cl.
CPC ........ *A61M 5/3232* (2013.01); *A61M 5/3234* (2013.01); *A61M 5/31511* (2013.01);
(Continued)

(58) Field of Classification Search
CPC .... A61M 2005/323; A61M 2005/3231; A61M 2005/3238; A61M 2005/5073; A61M 5/31511; A61M 5/3232; A61M 5/345
See application file for complete search history.

(56) References Cited

U.S. PATENT DOCUMENTS

| 4,252,118 A | 2/1981 | Richard et al. |
| 5,201,720 A | 4/1993 | Borgia et al. |

(Continued)

FOREIGN PATENT DOCUMENTS

| WO | 95/30445 A1 | 11/1995 |
| WO | 01/30428 A1 | 5/2001 |

(Continued)

OTHER PUBLICATIONS

International Search Report for International Patent Application No. PCT/AU2008/000971 (Sep. 8, 2008).

(Continued)

*Primary Examiner* — Rebecca E Eisenberg
(74) *Attorney, Agent, or Firm* — LeClairRyan, a Professional Corporation

(57) ABSTRACT

A retractable syringe, plunger and releasable needle assembly including a retractable needle, a needle seal, a retaining member and an ejector member. The retaining member has a mating surface for mounting to a complementary mating surface of an interior wall of a syringe barrel. The plunger comprises a plunger outer, a plunger rod frangibly connected to a controlling member, a spring and a unitary plunger seal capable of engaging the retractable needle, wherein the plunger rod, plunger outer and the controlling member
(Continued)

co-operate to releasably maintain the spring in an initially compressed state. After delivery of fluid contents of the syringe, the plunger forces the ejector member to release the retractable needle from the retaining member. Decompression of the spring at the end of depression of the plunger facilitates retraction of the retractable needle when engaged with the unitary plunger seal.

22 Claims, 19 Drawing Sheets

Related U.S. Application Data

(60) Provisional application No. 61/012,643, filed on Dec. 10, 2007.

(51) Int. Cl.
    *A61M 5/315*     (2006.01)
    *A61M 5/34*     (2006.01)
    *A61M 5/31*     (2006.01)
    *A61M 5/50*     (2006.01)

(52) U.S. Cl.
CPC .......... *A61M 5/3202* (2013.01); *A61M 5/345* (2013.01); *A61M 2005/3103* (2013.01); *A61M 2005/323* (2013.01); *A61M 2005/3231* (2013.01); *A61M 2005/3238* (2013.01); *A61M 2005/5073* (2013.01); *A61M 2205/581* (2013.01); *A61M 2205/582* (2013.01); *Y10T 29/49826* (2015.01)

(56) References Cited

U.S. PATENT DOCUMENTS

| | | |
|---|---|---|
| 5,211,628 A | 5/1993 | Marshall |
| 5,407,431 A | 4/1995 | Botich et al. |
| 5,885,257 A | 3/1999 | Badger |
| 6,206,853 B1 | 3/2001 | Bonnet |
| 6,206,857 B1 | 3/2001 | Chen |
| 6,716,191 B2 | 4/2004 | Sergio |
| 6,863,659 B2 | 3/2005 | Sharpe |
| 2003/0187400 A1 | 10/2003 | Liao |
| 2005/0228344 A1 | 10/2005 | Fitzgerald |
| 2006/0129096 A1 | 6/2006 | Wright |
| 2006/0189931 A1 | 8/2006 | Riemelmoser |
| 2007/0066936 A1 | 3/2007 | Lam |

FOREIGN PATENT DOCUMENTS

| | | | |
|---|---|---|---|
| WO | 03/097133 A1 | | 11/2003 |
| WO | 2004-082747 A1 | | 9/2004 |
| WO | 2005/089831 A1 | | 9/2005 |
| WO | 2006108243 | * | 10/2006 |

OTHER PUBLICATIONS

Written Opinion of the International Searching Authority for International Patent Application No. PCT/AU2008/000971 (Sep. 4, 2008).

* cited by examiner

PREFILLED RETRACTABLE SYRINGE, PLUNGER AND NEEDLE ASSEMBLY

This application is a continuation of U.S. patent application Ser. No. 12/666,448, filed Oct. 1, 2010, that claims the benefit under 35 U.S.C. §371 National Stage of International Application No. PCT/AU2008/000971, filed Jul. 2, 2008, that claims the benefit under 35 U.S.C. §119(e) of U.S. Provisional Application No. 61/012,643, filed Dec. 10, 2007, and of Australian Application No. 2007903565, filed Jul. 2, 2007 with the Australian Patent Office, which are hereby incorporated by reference in their entirety.

FIELD OF THE INVENTION

THIS INVENTION relates to syringes. More particularly, this invention relates to a retractable syringe that includes a needle retraction mechanism to prevent re-use of the syringe and/or needle stick injury, wherein the needle retraction mechanism acts in a controlled manner.

BACKGROUND OF THE INVENTION

The practice of sharing syringes without adequate sterilization between successive users is a major contributor to the transfer of Human Immunodeficiency Virus (HIV) and Hepatitis with subsequent severe repercussions for the sufferer and at a high cost to society for supporting and providing medical attention to sufferers.

Furthermore, health professionals may be exposed to used syringes which can lead to inadvertent needlestick injuries and possible exposure to infective pathogens or other contaminants.

In response to this problem, retractable syringes have been developed with the aim of preventing syringe re-use and/or needlestick injury by used syringes.

SUMMARY OF THE INVENTION

In developing retractable syringes, particularly for mass production and distribution, an objective is to reduce manufacturing costs and/or maintain ease of use and/or syringe safety. These are important factors if safety syringes are to be available for mass consumption, particularly in third world countries with low health budgets.

Accordingly, a preferred object of the invention is to provide a user friendly and safe retractable syringe while keeping manufacturing costs to a minimum, thereby facilitating mass distribution of retractable syringes.

It is yet another preferred object to provide a retractable syringe which efficiently delivers fluid contents, thereby minimizing wastage of said fluid contents.

It is a particularly preferred object to provide a prefilled retractable syringe.

In a first aspect, the invention provides a plunger for a retractable syringe, said plunger comprising a plunger rod, a plunger outer, a controlling member and a biasing member, wherein the plunger rod, plunger outer and the controlling member co-operate to releasably maintain said biasing member in an initially energized state.

In a second aspect, the invention provides a retractable syringe comprising a barrel; a retractable needle; and a plunger engageable with said retractable needle, said plunger comprising a plunger rod, a plunger outer, a controlling member and a biasing member, wherein the plunger rod, plunger outer and the controlling member co-operate to releasably maintain said biasing member in an initially energized state.

In a third aspect, the invention provides a releasable needle retaining system comprising: a retractable needle and a retaining member mounted to an interior wall of a syringe barrel, or formed integrally therewith, said retaining member capable of initially retaining said retractable needle at a needle end of said barrel until said retractable needle is engaged by a plunger to facilitate retraction of said retractable needle.

In a fourth aspect, the invention provides a retractable syringe comprising a barrel; a releasable needle retaining system that comprises a retractable needle and a retaining member mounted to an interior wall of a syringe barrel, or formed integrally therewith; and a plunger engageable with said retractable needle; said retaining member capable of initially retaining said retractable needle at a needle end of said barrel until said retractable needle is engaged by said plunger to facilitate retraction of said retractable needle.

Suitably, the syringe according to the aforementioned aspects is a prefilled syringe.

Preferably, the plunger further comprises a plunger seal which is capable of engaging said retractable needle.

In one preferred embodiment, the plunger seal is a unitary plunger seal.

Suitably, the controlling member facilitates control of the rate of retraction of said retractable needle when engaged with said plunger and is removable from said plunger following needle retraction.

Suitably, said controlling member comprises one or more mating portions that initially engage said plunger outer to facilitate maintaining said biasing member in an initially energized state.

In one embodiment, said controlling member comprises one or more arm members that initially engage said plunger outer to facilitate maintaining said biasing member in an initially energized state.

In another embodiment, said controlling member comprises one or more cutaways, notches or recesses that initially engage said plunger outer to facilitate maintaining said biasing member in an initially energized state.

Suitably, retraction of said retractable needle is facilitated by said biasing member, such as a spring, elastic or other device for storing energy.

Preferably, the biasing member is a spring.

In a preferred embodiment, the spring is initially compressed so that decompression of said spring facilitates retraction of said retractable needle.

In a preferred embodiment, the retaining member comprises a mating surface complementary to a mating surface of the interior wall of the syringe barrel.

In a preferred form, the releasable needle retaining system further comprises a needle seal.

Preferably, the retractable needle comprises a retractable needle body and a cannula.

In a particularly preferred embodiment, the releasable needle retaining system further comprises an ejector member which facilitates release of the retractable needle from the retaining member to facilitate retraction of said retractable needle when engaged by said plunger.

According to the aforementioned aspects, typically, although not exclusively, the barrel is formed of glass.

Preferably, said barrel further comprises a collar having one or more releasing members that facilitate release of said controlling member from said plunger outer.

Preferably, said syringe or said plunger comprises at least one locking system which prevents re-use of the syringe at the end of needle retraction.

In one embodiment, one said locking system comprises respective elements of said barrel and said plunger outer. Preferably, according to this embodiment the locking system comprises elements of said collar and said plunger outer.

In another embodiment, another said locking system comprises elements of said plunger rod and said plunger outer.

Preferably, said syringe comprises both said locking systems.

In a particularly preferred, non-limiting embodiment, the invention provides a prefilled retractable syringe comprising:
 (i) a glass barrel that comprises an interior wall and a collar having a releasing ring;
 (ii) a releasable needle retaining system that comprises: a needle assembly that comprises a retractable needle and a needle seal; a retaining member that comprises a mating surface complementary to a mating surface of said interior wall; and an ejector member for releasing the retractable needle from the retaining member;
 (iii) a plunger engageable with said retractable needle, said plunger comprising, a plunger outer, a plunger rod frangibly connected to a controlling member comprising one or more mating portions, a spring and a unitary plunger seal capable of engaging said retractable needle, wherein the plunger rod, plunger outer and the controlling member co-operate to releasably maintain said spring in an initially compressed state, said one or more mating portions of said controlling member engaging said plunger outer until said releasing ring disengages said one or more mating portions from said plunger outer at the end of depression of said plunger to facilitate decompression of said spring and retraction of said retractable needle when engaged with said unitary plunger seal; and
 (iv) locking systems respectively formed between: elements of the plunger outer and the collar; and elements of the plunger rod and the plunger outer; operable to prevent re-use of the syringe after needle retraction.

It will also be appreciated that in other aspects the invention also relates to a method of assembly of the aforementioned plunger, releasable needle retaining assembly and/or syringe and to a method of use of the aforementioned syringe.

In a preferred embodiment, the method of assembly of the syringe includes the sequential steps of:
 (i) mounting the releasable needle retaining assembly to a syringe barrel;
 (ii) filling the barrel with fluid contents;
 (iii) inserting the plunger seal into the barrel; and
 (iv) coupling the plunger to the plunger seal.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWINGS

Non-limiting embodiments of the invention are described herein with reference to the following drawings wherein.

DETAILED DESCRIPTION OF THE PREFERRED EMBODIMENT

Figure 1:
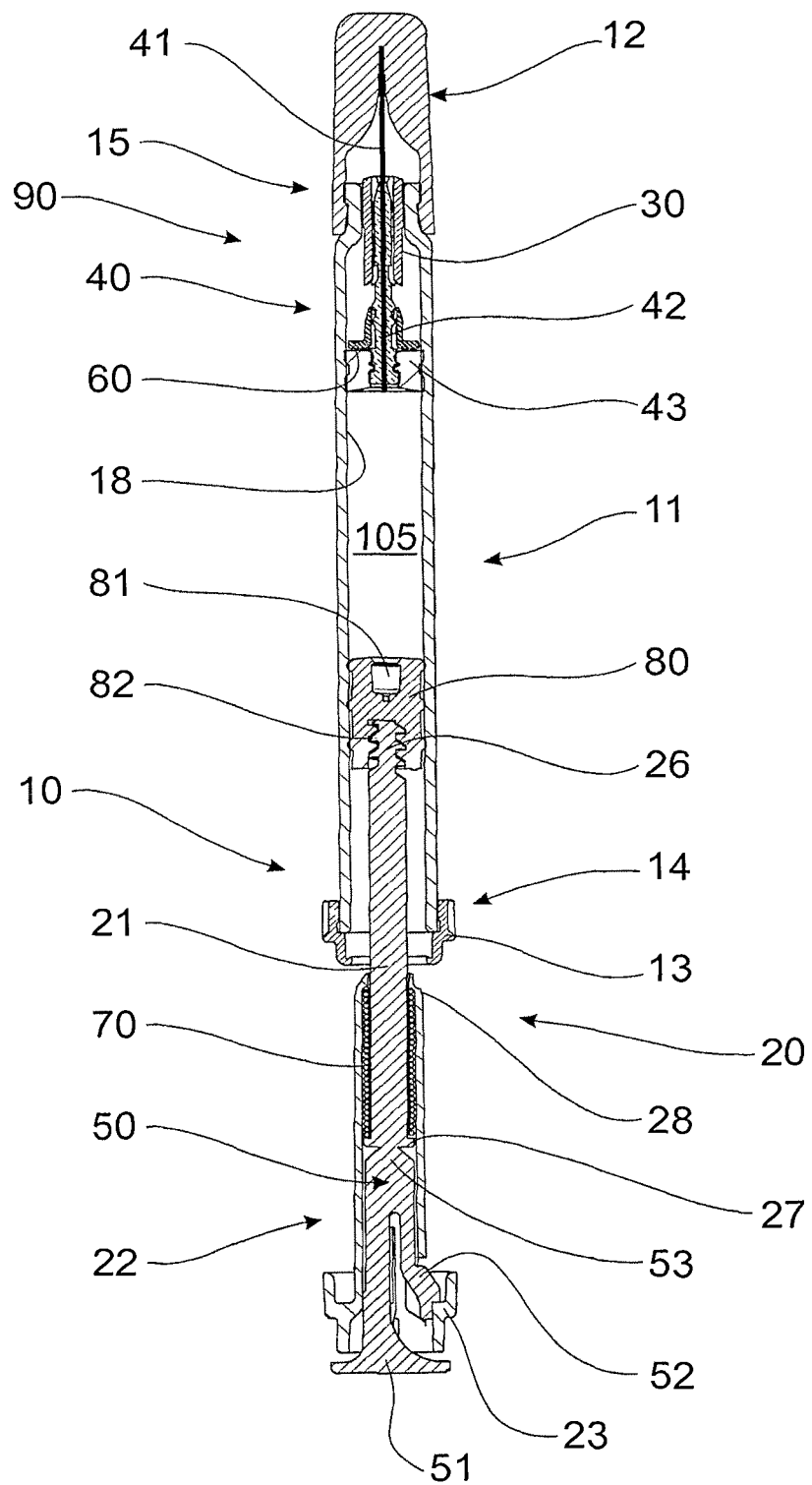
FIG. 1 is a sectional view of an embodiment of a retractable syringe.

Referring to FIG. 1, an embodiment of retractable syringe 10 comprises barrel 11 and plunger 20 having plunger seal 80 mounted to plunger 20. Barrel 11 is formed of glass and comprises plunger end 14 at which is located collar 13, and needle end 15 in which is mounted releasable needle retaining system 90 comprising retractable needle 40 that comprises cannula 41 and retractable needle body 42, needle seal 43, ejector member 60 and retaining member 30. At needle end 15 is also protective cover 12 for cannula 41. Collar 13 may be mounted or otherwise fitted to barrel 11, or co-moulded with barrel 11.

Barrel 11 further comprises inside wall 18 which, together with needle seal 43 and plunger seal 80 define fluid space 105 inside barrel 11. Retaining member 30 has a relatively smooth outside diameter (OD) comprising a mating surface which fits flush with complementary mating surface of internal wall 18 of barrel. Preferably, retaining member 30 is glued or otherwise adhered to glass barrel 11. This arrangement obviates the need to include complementary grooves, ribs or co-moulding (for example) to hold retaining member 30 in barrel 11, thereby improving the ease with which retractable syringe 10 is manufactured and assembled.

In use, plunger 20 is movable axially into fluid space 105 to facilitate delivery of fluid contents of retractable syringe 10. In a preferred embodiment, fluid space 105 is prefilled with the fluid contents to be delivered by retractable syringe 10. A non-limiting example of fluid contents is a low molecular weight heparin such as enoxaparin sodium (e.g. Lovenox®).

Figure 2:
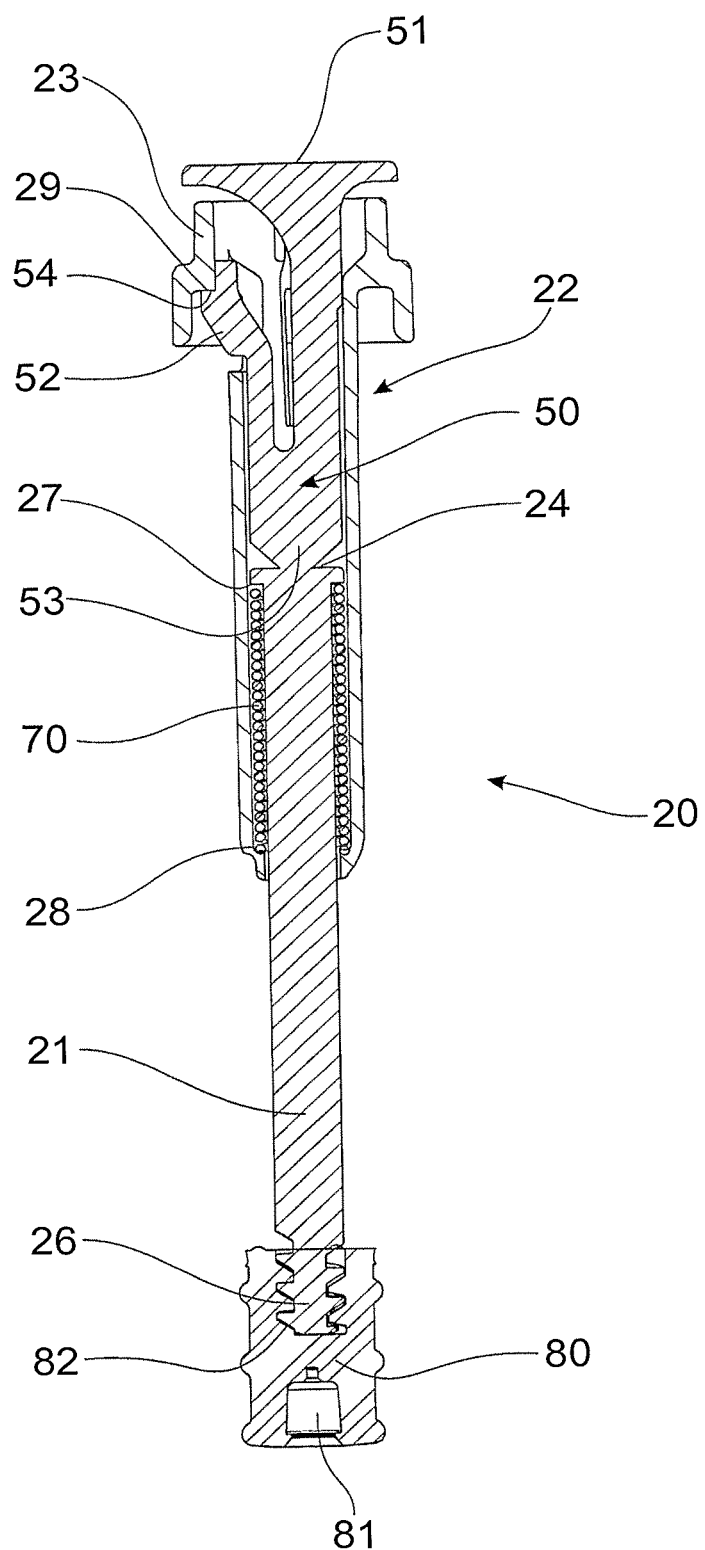
FIG. 2 is a sectional view of an embodiment of a plunger.
Figure 3:
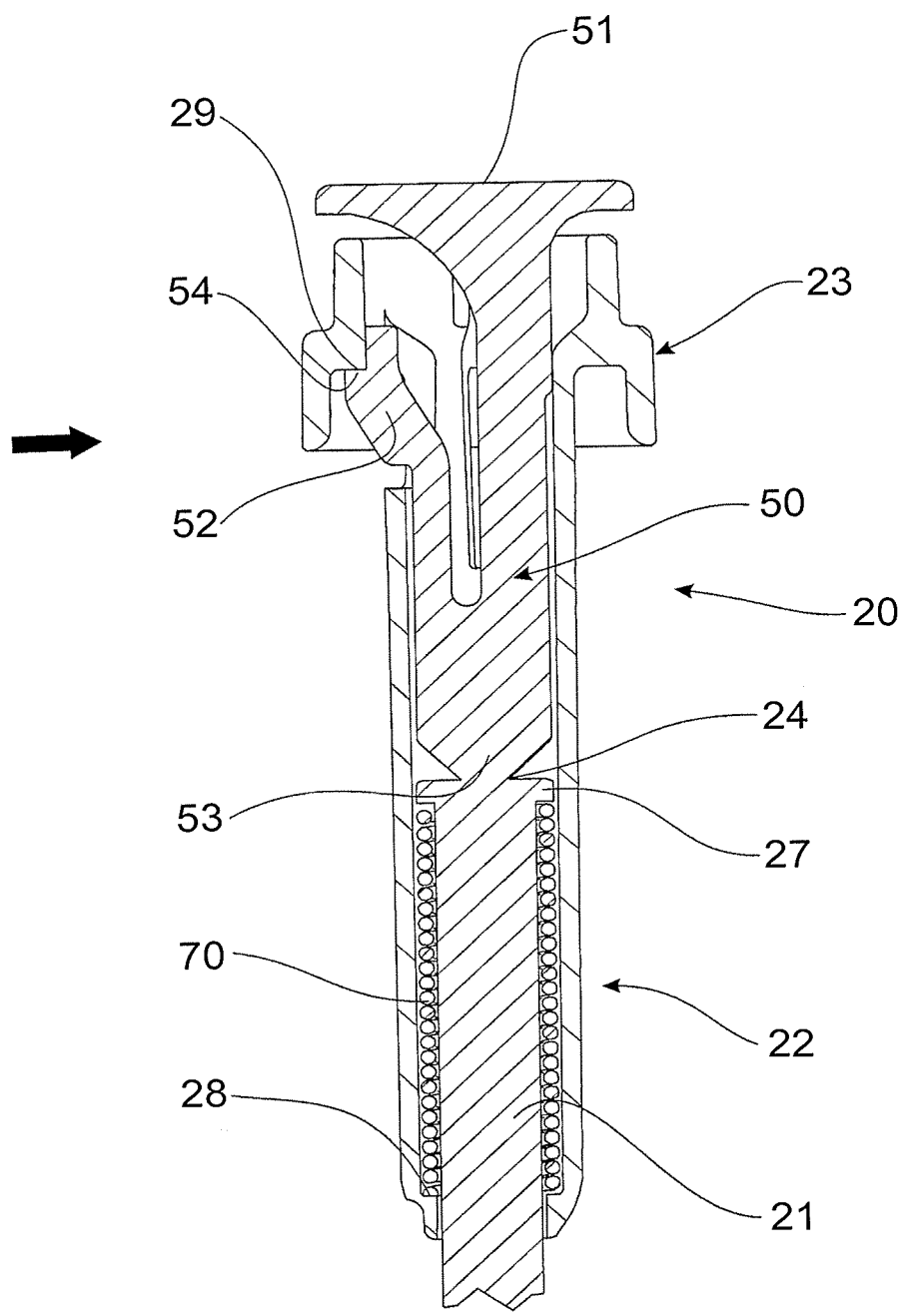
FIG. 3 is another sectional view of an embodiment of a plunger.

Referring particularly to FIG. 2 and FIG. 3, plunger 20 comprises plunger rod 21 and plunger outer 22 having cap member 23. Releasably engaged with plunger 20 is controlling member 50 comprising button 51, arm 52 and shaft 53. Plunger 20 further comprises compressed spring 70 which is mounted between plunger rod 21 and plunger outer 22, held in a compressed state between annular ledge 27 of plunger rod 21 and base 28 of plunger outer 22.

Plunger rod 21 further comprises seal engaging member 26, which in this embodiment is a screw threaded projection, which engages complementary recess 82 of plunger seal 80. In an alternative embodiment, seal engaging member 26 may be in the form of a snap lock projection that engages a complementary recess in plunger seal 80.

As best shown in FIG. 3, controlling member 50 is releasably coupled to plunger rod 21 by way of shaft 53 which comprises frangible junction 24 with plunger rod 21. The frangible engagement between controlling member 50 and plunger rod 21 applies minimal stress to frangible junction 24.

Controlling member 50 also releasably engages plunger outer 22, which engagement retains spring 70 in an initially compressed state held between annular ledge 27 of plunger rod 21 and base 28 of plunger outer 22. Initially ledge 54 of arm 52 abuts rim 29 of cap member 23 of plunger outer 22 to thereby retain controlling member 50 and prevent axial movement of controlling member relative to plunger outer 22. However, arm 52 of controlling member 50 is resiliently flexible and movable in the direction of the solid arrow shown in FIG. 3, which will allow disengagement of controlling member 50 from plunger outer 22 to facilitate decompression of spring 70, as will be described in detail hereinafter.

Figure 4:
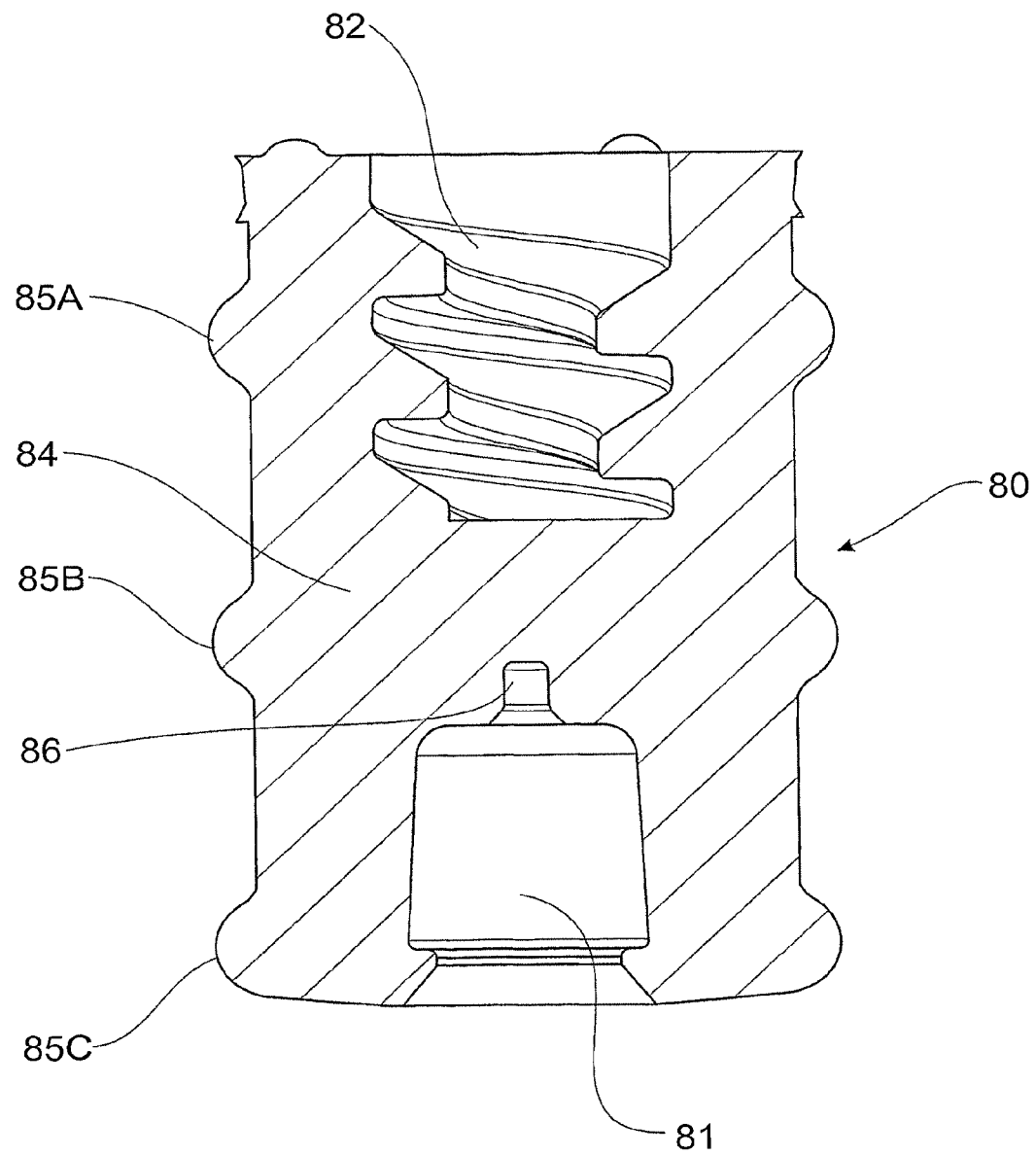
FIG. 4 is a sectional view of an embodiment of a unitary plunger seal.

Referring now to FIG. 4, plunger seal 80 is of unitary construction and is mounted to plunger 20 to thereby provide a fluid seal between plunger 20 and inside wall 18 of barrel 11. Plunger seal 80 comprises seal body 84 and circumferential ribs 85A, B, C that effect a fluid-tight seal between plunger 20 and inside wall 18 of barrel 11.

Plunger seal 80 further comprises recessed seat 81 that receives base 405 of retractable needle body 42 and also needle recess 86 that receives cannula end 141 towards the end of plunger 20 depression, prior to retraction of retractable needle 40, as will be described hereinafter.

Figure 5:
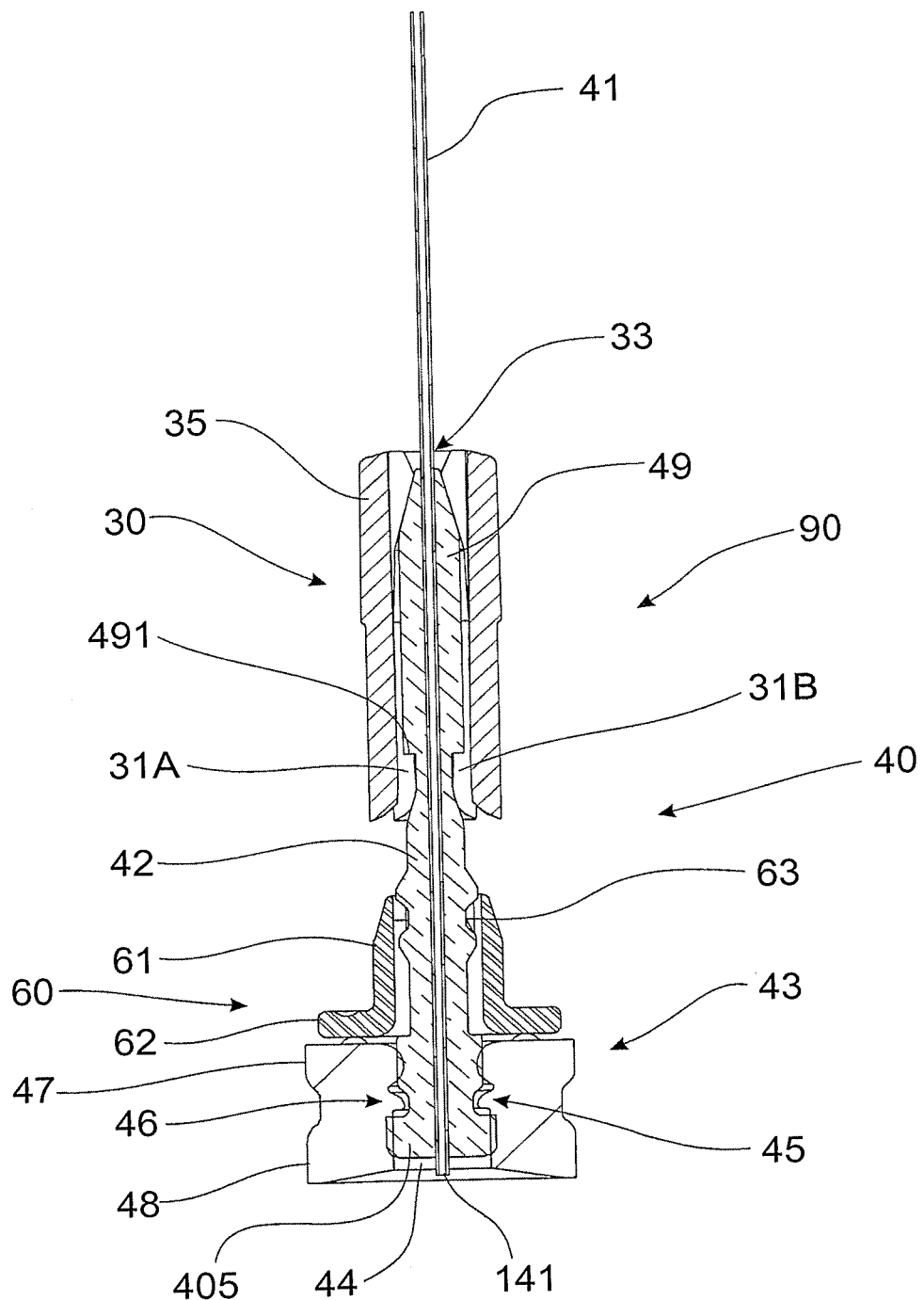
FIG. 5 is a sectional view of an embodiment of a needle seal, retractable needle, ejector member and a retaining member.
Figure 6:
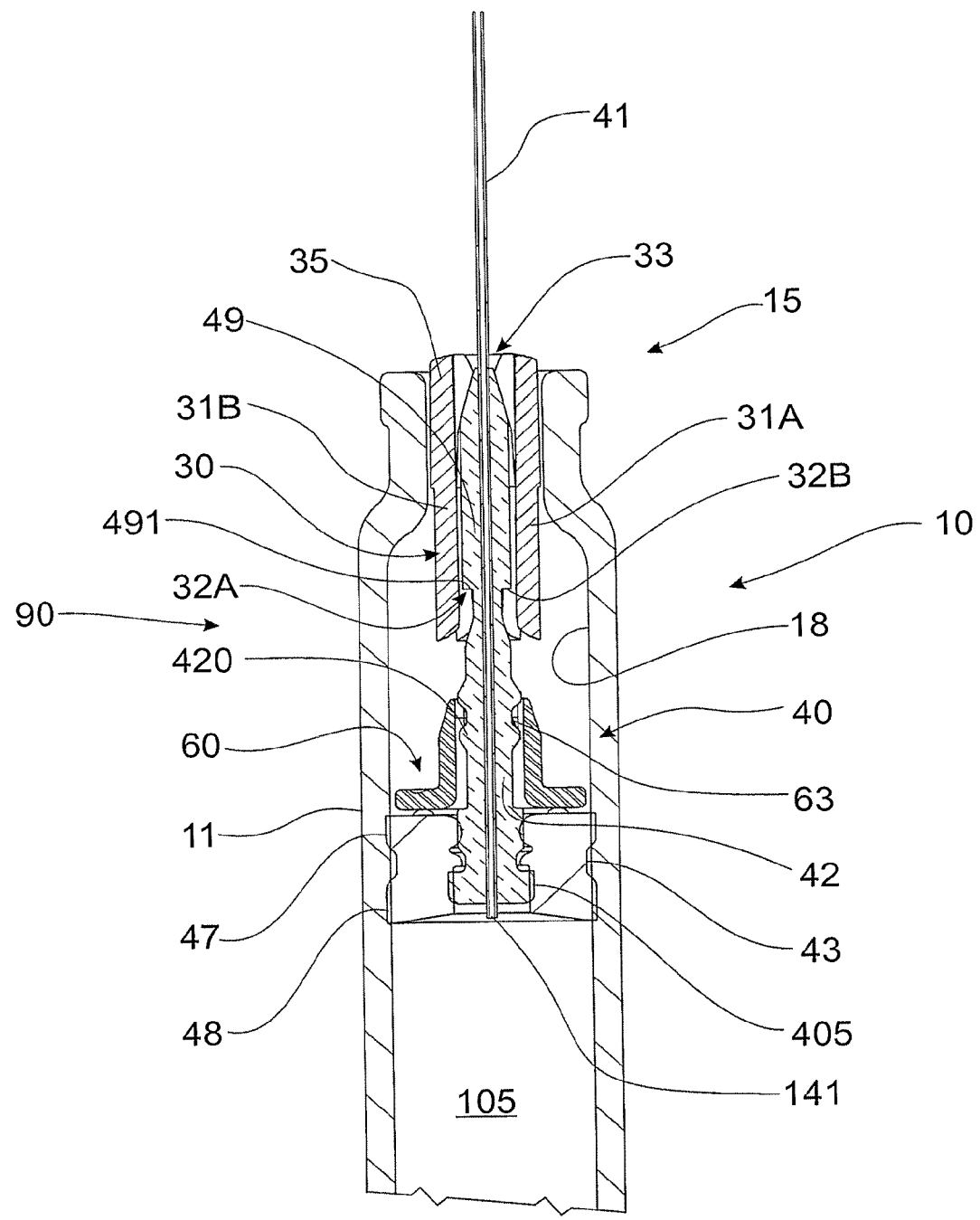
FIG. 6 is another sectional view of an embodiment of a needle seal, retractable needle, ejector member and a retaining member mounted at a needle end of a syringe barrel showing engagement between the barrel and the retaining member.

In FIGS. 5 and 6, protective cover 12 has been removed and retractable syringe 10 is ready for use. At needle end 15 of barrel 11 is mounted releasable needle retaining system 90 comprising retractable needle 40 having cannula 41 and retractable needle body 42 and needle seal 43. End 141 of cannula 41 communicates with fluid contents in fluid space 105 of barrel 11. As evident from FIG. 5, needle seal 43 comprises complementary steps 46 forming bore 44, that respectively receive steps 45 of retractable needle body 42, so that base 405 of retractable needle body 42 initially sits inside bore 44. In a similar manner to the needle seal described in International Publication WO 2006/108243 and as best seen in FIG. 5, it is advantageous for retractable needle body 42 to have a tapered cross section, tapering toward cannula 41, and comprise plurality of steps 45. This stepped configuration means that the amount of movement required to dislodge retractable needle 40 from needle seal 43 is minimized. The taper may assist centering of retractable needle 40 when withdrawn from needle seal 43 in that resistance to withdrawal of retractable needle 40 effectively reduces as cross-sectionally tapered retractable needle body 42 is withdrawn through bore 44 of needle seal 43.

Needle seal 43 also has annular rib 47 and annular base 48 that co-operate with inside wall 18 of barrel 11 to facilitate improved sealing performance and prevent inadvertent leakage of fluid contents.

As previously described, retaining member 30 is mounted inside needle end 15 of barrel 11, which as best seen in FIG. 6, has a "smooth" mating surface to facilitate adhesion into the "smooth" mating surface of inside wall 18 of needle end 15 of barrel 11. This is a preferred embodiment when retractable syringe 10 is made of glass. In an alternative embodiment particularly suited to a plastic retractable syringe 10, retaining member 30 is mounted by a circumferential rib (not shown) on inside wall 18 of barrel 11 engaging a circumferential groove (not shown) on retaining member 30. In another alternative embodiment of a plastic retractable syringe 10, retaining member 30 could be co-moulded into needle end 15 of barrel 11.

Also at needle end 15 is ejector member 60, which comprises ejector ring 61 and base 62. Ejector member 60 engages circumferential recess 420 on retractable needle body 42 via annular detent 63. Ejector member 60 is not fixed or positively mounted or engaged with needle seal 43, but simply bears against needle seal 43, unlike the corresponding arrangement in International Publication WO 2006/108243. Alternatively, needle seal 43 and ejector member 60 may be co-moulded as a unitary structure.

Figure 7:
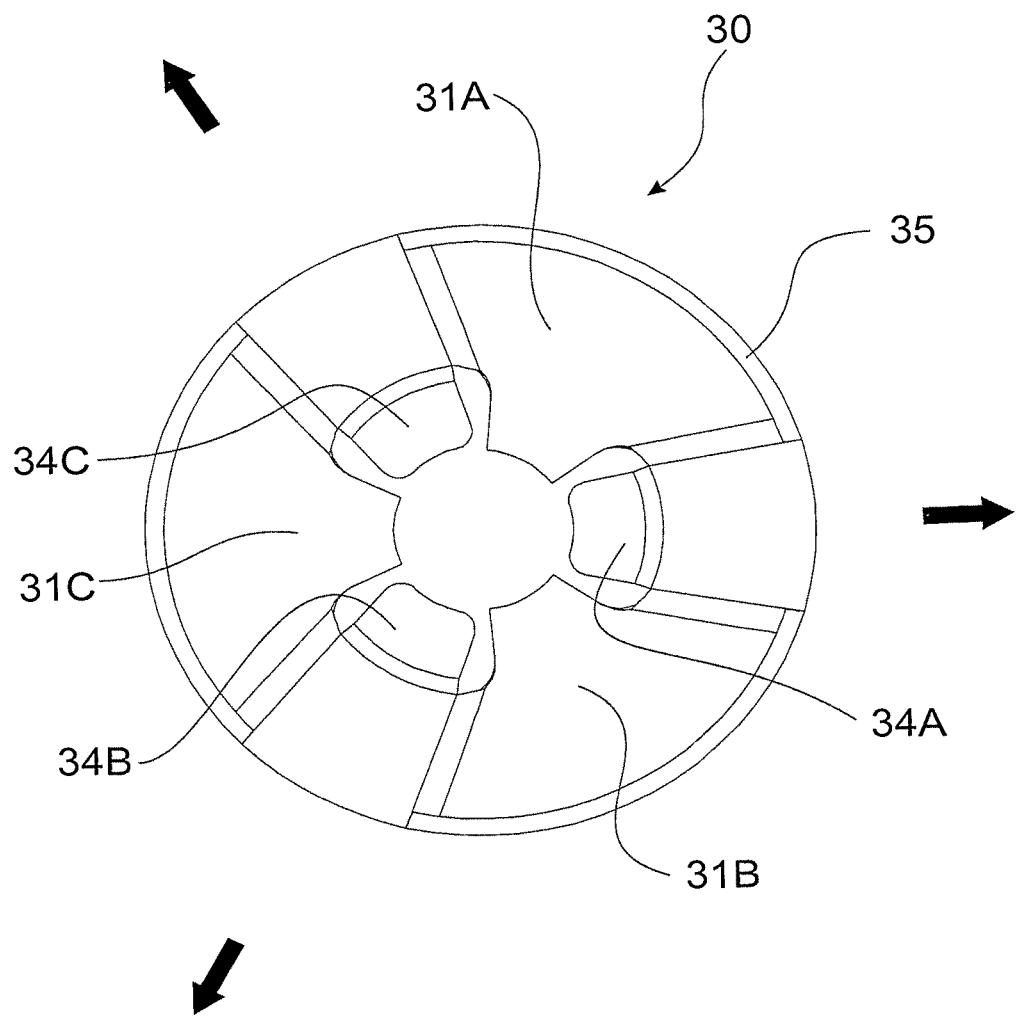
FIG. 7 is a plan view of an embodiment of a retaining member.
Figure 8:
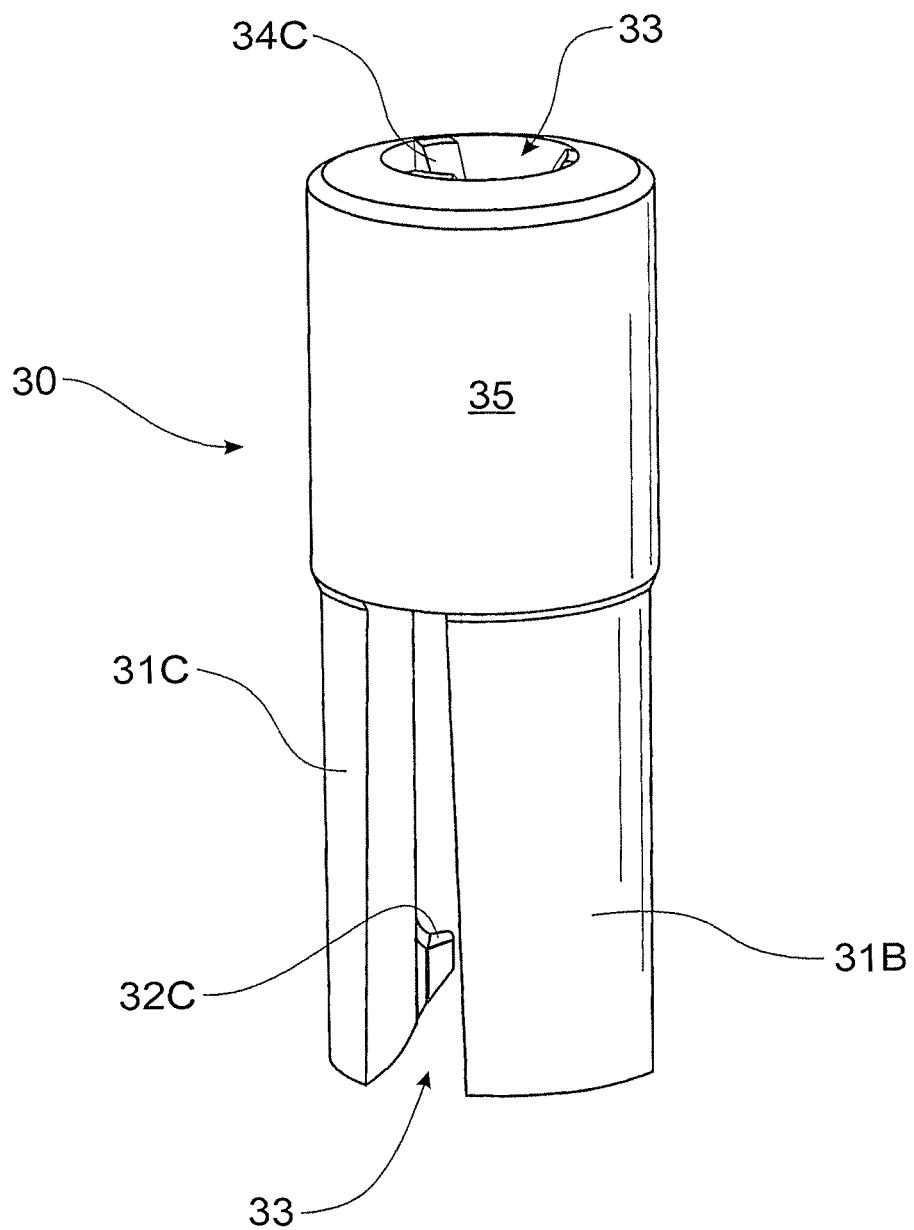
FIG. 8 is a side perspective view of an embodiment of a retaining member.

Referring again to FIG. 6 and also to FIG. 7 and FIG. 8, cannula 41 and retractable needle body 42 protrudes through central bore 33 of retaining member 30. Retaining member 30 comprises cylindrical body 35 and fingers 31A, 31B, 31C that respectively comprise angled faces 32A, 32B, 32C (visible in FIG. 8) that abut ledge 491 of head 49 of retractable needle body 42 to releasably hold retractable needle 40 in position during operation of retractable syringe 10. Cylindrical body 35 of retaining member 30 further comprises internal tapered bosses 34A, 34B and 34C that engage head 49 of retractable needle body 42 to prevent retractable needle body 42 pushing out of barrel 11.

The sequence of events whereby retractable needle 40 is disengaged from retaining member 30 to facilitate retraction of retractable needle 40 is shown in FIG. 9A-C.

Typically, retractable syringe 10 is provided prefilled with fluid contents for delivery. Therefore, plunger 20 is provided in an initial position ready for depression to deliver the fluid contents of the retractable syringe 10.

As seen in FIG. 9A-C, at or near the end of plunger 20 depression (direction indicated by solid arrow), plunger 20 moves plunger seal 80 coupled thereto against needle seal 43 at needle end 15 of barrel 11. This moves ejector member 60 so that it engages retaining member 30. Plunger 20 continues to move in the direction of the solid arrow so that recessed seat 81 receives base 405 of retractable needle body 42 and needle recess 86 receives cannula end 141. This effectively couples retractable needle body 42 to plunger 20.

A feature of this design is that plunger seal 80 "squeezes out" the last of the delivered fluid as base 405 of retractable needle body 42 engages recessed seat 81. Testing has shown that deadspace (amount of fluid left in retractable syringe 10 after injection) averages less than 0.001 g, which is more than acceptable for drug delivery.

Figure 9:
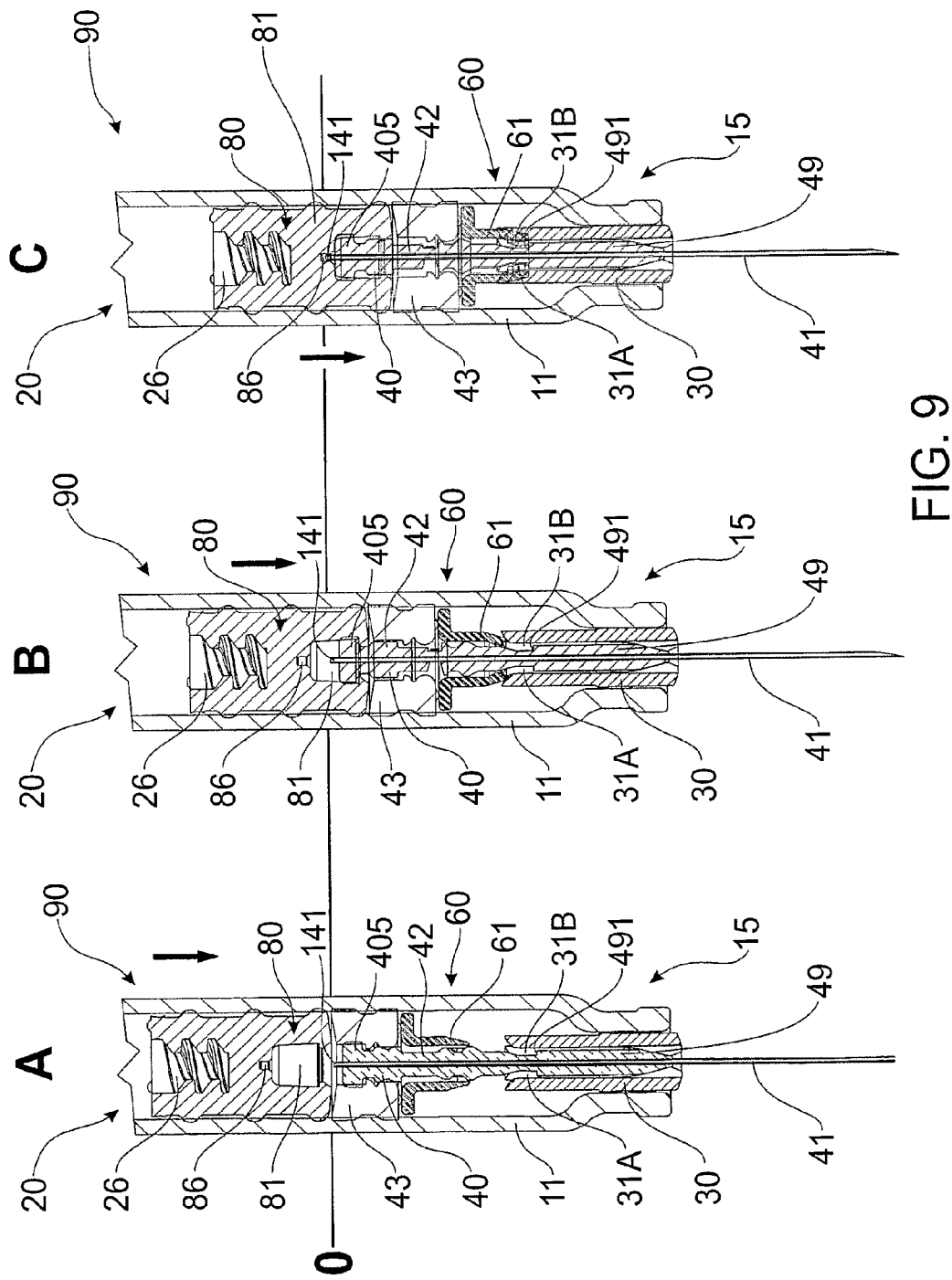
FIG. 9A-C are sectional views progressively showing engagement of a retractable needle by a unitary plunger seal prior to retraction.

Continued axial movement of plunger 20 in the direction of the solid arrow in FIG. 9 causes plunger seal 80 to bear against and force needle seal 43 further towards needle end 15 of barrel 11 so that ejector ring 61 of ejector member 60 displaces fingers 31A, 31B, 31C of retaining member 30 out from behind ledge 491 of head 49 of retractable needle body 42 in the direction shown by solid arrows in FIG. 7. This releases retractable needle 40 for retraction. One particular advantage of this releasable needle retaining system 90 is that ejector member 60 permanently deforms fingers 31A, 31B, 31C of retaining member 30 to facilitate preventing re-use of the syringe after release of retractable needle 40.

Figure 10:
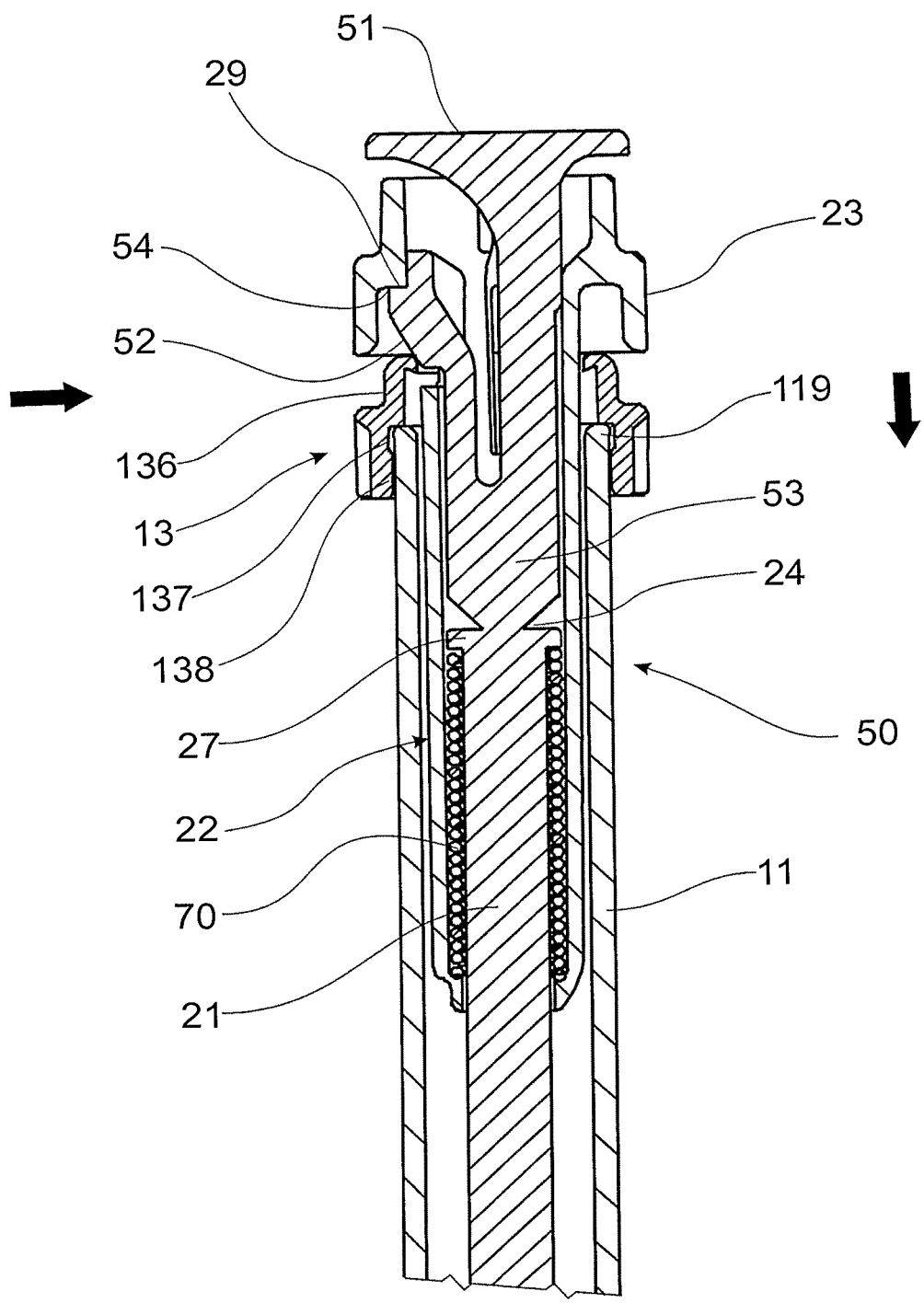
FIG. 10 is a sectional view showing engagement between a plunger outer and controlling member toward the end of plunger depression.

In order for retractable needle 40 to retract, compressed spring 70 must decompress, which is facilitated by plunger rod 21 disengaging from plunger outer 22. Referring to FIG. 10, axial movement of plunger 20 in the direction of the solid vertical arrow brings arm 52 of controlling member 50 to bear against release ring 136 of collar 13 at plunger end 14 of barrel 11 (which is not shown for clarity). Release ring 136 may be mounted or otherwise fitted to barrel 11, or may be co-moulded with collar 13 and barrel 11.

Figure 11:
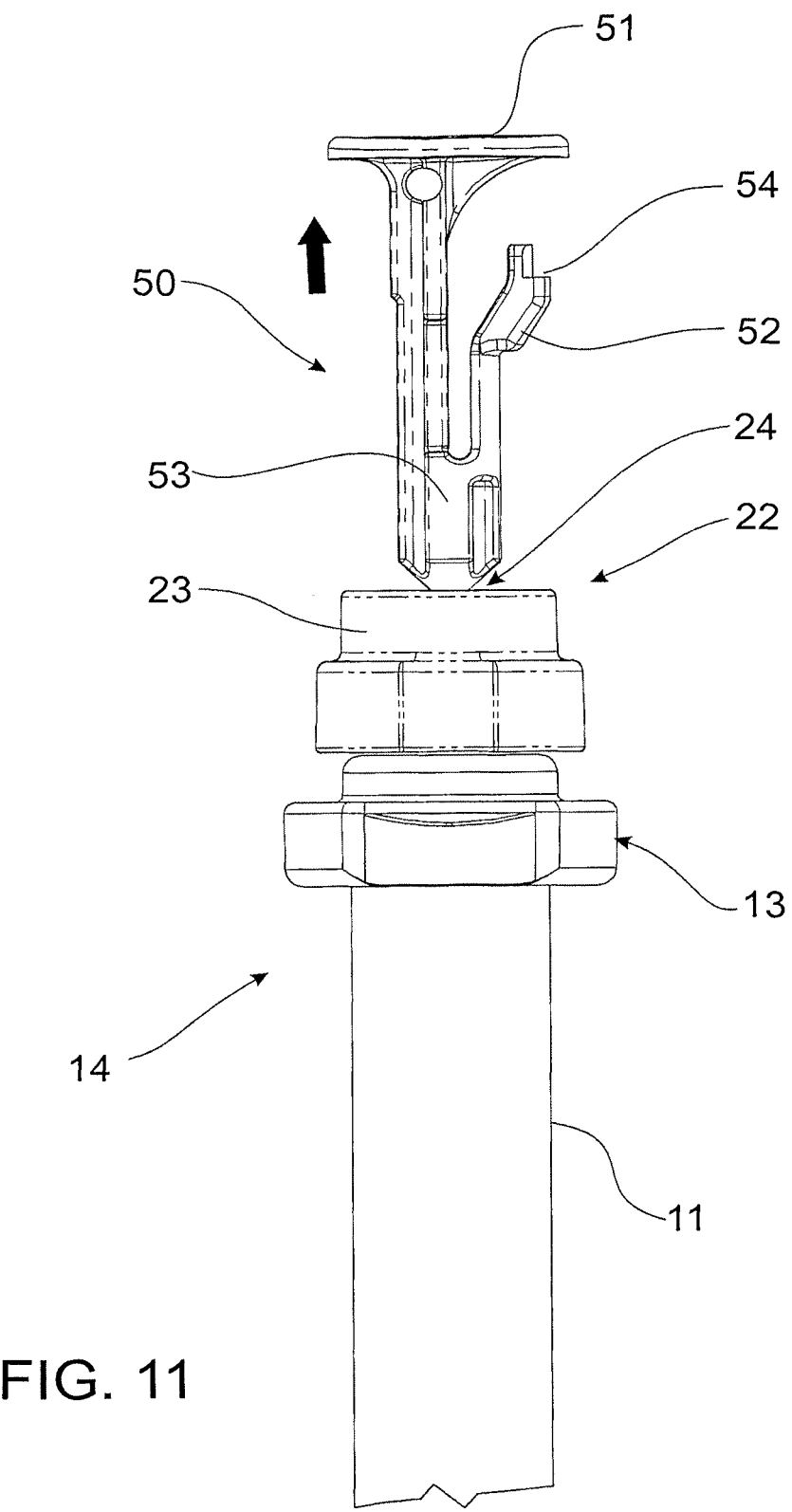
FIG. 11 is a side view of a syringe showing retraction of a plunger rod and controlling member after disengagement between a plunger outer and the controlling member and spring decompression.

Release ring 136 forces arm 52 to move laterally in the direction of the horizontal solid arrow and out of engagement with rim 29 of cap member 23 of plunger outer 22. This disengagement allows compressed spring 70 to decompress and push against ledge 27 of plunger rod 21 to thereby retract plunger rod 21 with controlling member 50 coupled thereto. This disengagement may also be accompanied by an audible and/or tactile signal (e.g. a "click") which indicates to the user that retraction will occur. As was described in FIG. 9, retractable needle 40 is coupled to plunger seal 80 and so retracts with plunger rod 21 in the direction of the arrow in FIG. 11 inside barrel 11, thereby being completely enveloped by, and contained within, barrel 11. While retraction of needle 40 is "automatically' driven by decompression of spring 70, the rate of retraction can be controlled by a user relaxing pressure (such as by way of thumb pressure) against button 51 of controlling member 50.

At the end of retraction of plunger rod 21 and retractable needle 40, controlling member 50 can be broken from plunger rod 21 at frangible junction 24 and manually removed from retractable syringe 10 and discarded as "clean" waste.

One advantage of this embodiment of plunger 20 is that when controlling member 50 is broken away from plunger rod 21, it constitutes a relatively short piece of material for subsequent "clean" waste disposal.

Another advantage of this embodiment of plunger 20 is that once controlling member 50 is broken away from plunger rod 21, there is little if any plunger 20 protruding externally from barrel 11 with which to attempt to force plunger 20 back into barrel 11 and re-engage the needle (not shown).

Retractable syringe 10 may further comprise first locking system 95A and second locking system 95B to prevent re-use of retractable syringe 10.

Figure 12:
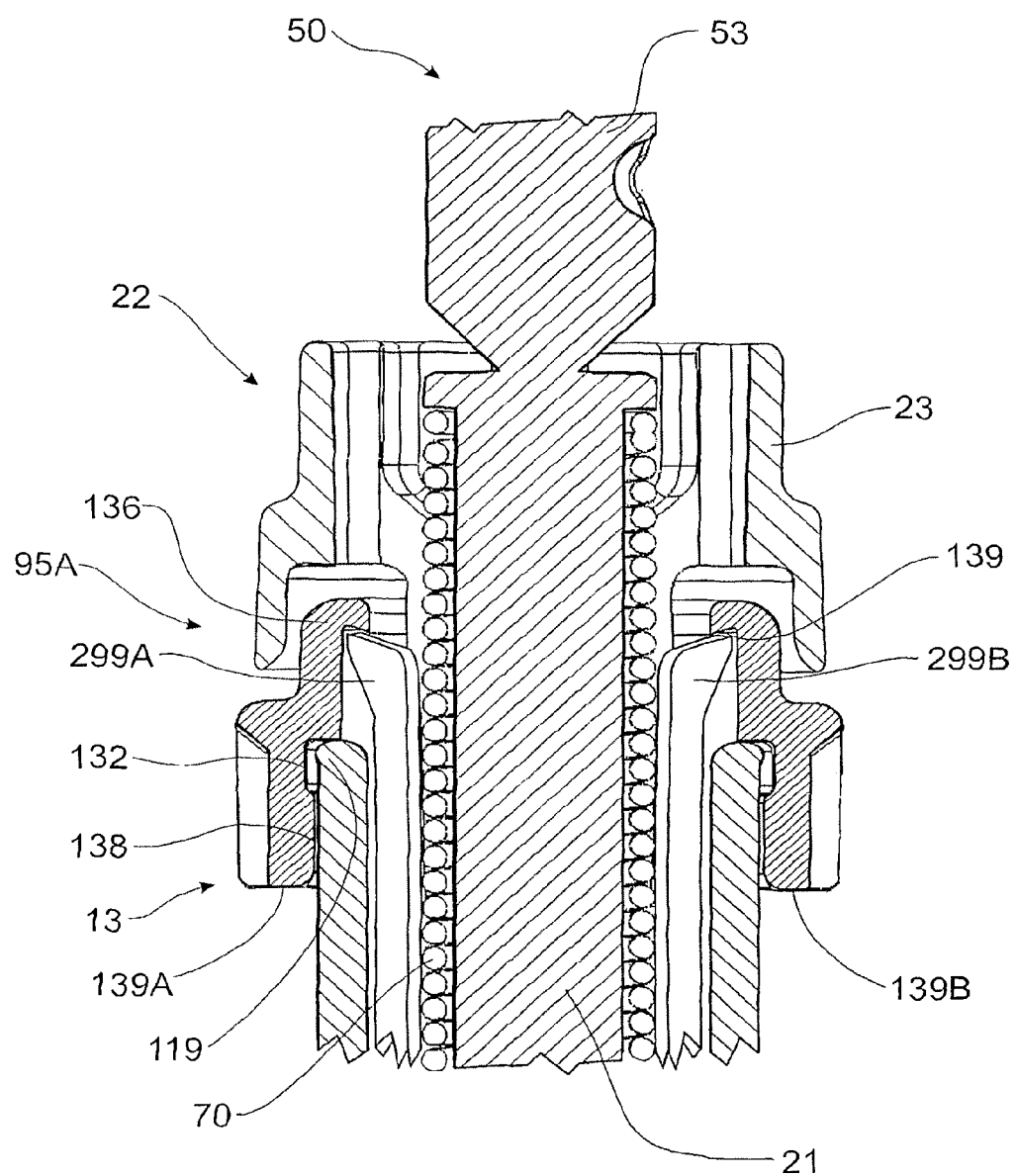
FIG. 12 is a sectional view of a locking system after needle retraction.

An embodiment of locking system 95A is shown in FIG. 12, where plunger outer 22 is locked into collar 13 to prevent withdrawal of plunger 20 from barrel 11 to extract retracted needle 40 and thereby prevents re-use of retractable syringe 10. In this embodiment, and as also evident in FIG. 10, complementary circumferential groove 137 of collar accommodates barrel lip 119. Adhesive or glue is applied to junction 138 between barrel 11 and collar 13. Plunger outer 22 comprises locking arms 299A, 299B that respectively engage locking rim 139 in collar 13. Locking arms 299A, 299B are oriented at approximately 150 degrees to each other to maximize strength of plunger outer 22.

Figure 13:
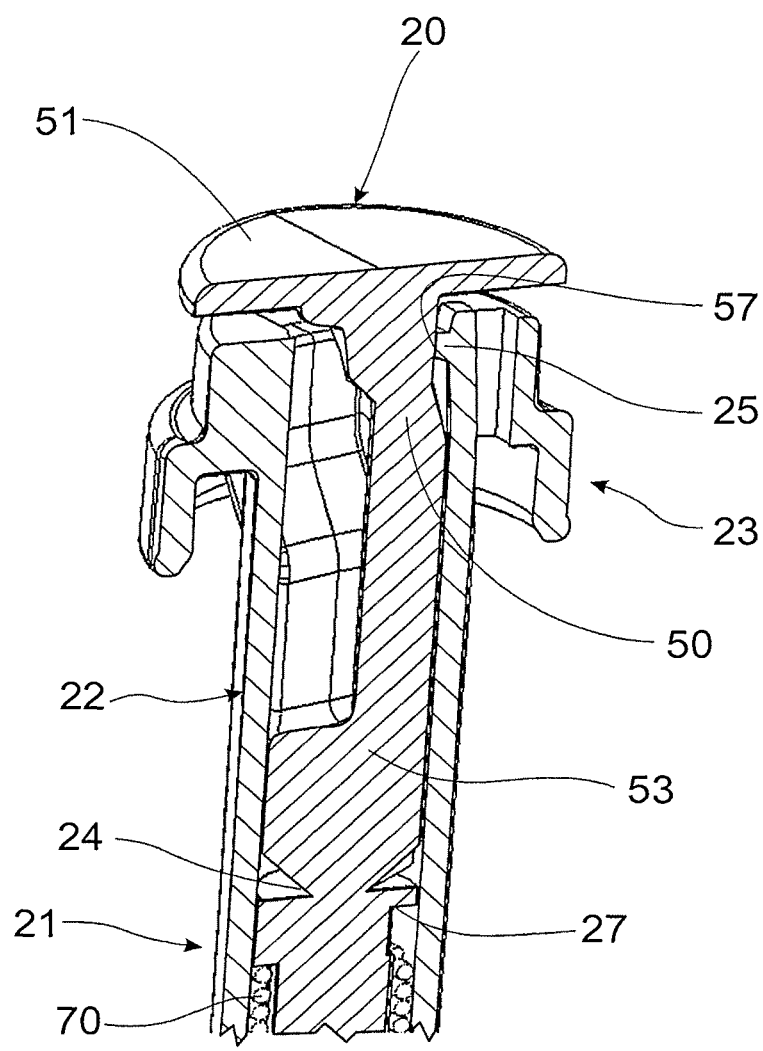
FIG. 13 shows a sectional view of another locking system prior to needle retraction.
Figure 14:
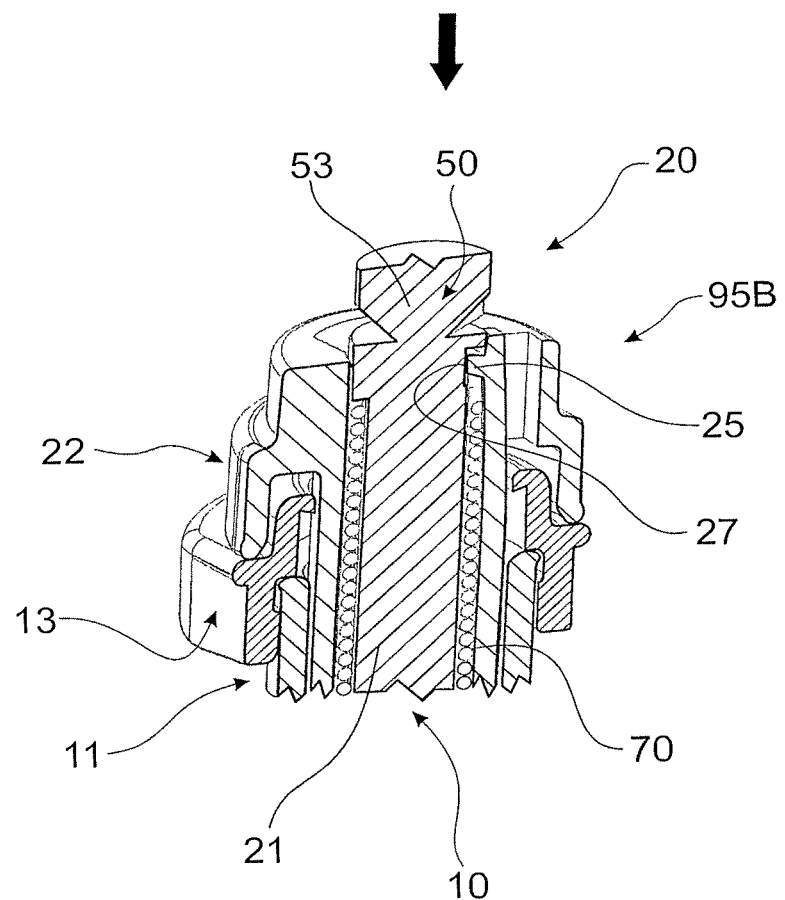
FIG. 14 shows a sectional view of said another locking system after needle retraction.

An embodiment of locking system 95B is shown in FIGS. 13 and 14.

Referring to FIG. 13 and FIG. 14, plunger 20 of retractable syringe 10 comprises plunger rod 21, controlling member 50 and plunger outer 22. Controlling member 50 further comprises recess 57 that initially engages flexible tab 25 of plunger outer 22. Plunger rod 21 and controlling member 50 are releasably connected by way of frangible junction 24. Preferably, recess 57 and flexible tab 25 are moulded into controlling member 50 and plunger outer 22, respectively.

Depression of plunger 20 to expel the fluid contents of retractable syringe 10 is essentially as hereinbefore described. Decompression of spring 70 along with the angled face and the height of the angled face of flexible tab 25 (i.e to prevent engaging in frangible junction 24) allows flexible tab 25 to pass over retracting controlling member 50 and plunger rod 21 until flexible tab 25 of plunger outer 22 engages notch 27 on plunger rod 21 to thereby form second locking system, as shown in FIGS. 13 and 14. Second locking system is arranged so that plunger rod 21 and controlling member 50 coupled thereto cannot move back towards the inside of plunger outer 22 in the direction of the solid arrows shown in FIG. 14. This prevents the retracted needle (not shown) from being re-exposed.

It will be appreciated that there are a number of manufacturing and design advantages provided by retractable syringe 10 and also variations that are contemplated within the broad scope of the present invention, primarily to assist manufacturing and design.

Typically, barrel 11 is formed of glass with lip 119 at plunger end 14 instead of finger grips. Collar 13 may have finger grips 139A, 139B incorporated therein and is glued or otherwise adhered to glass barrel 11 as previously described (as seen in FIGS. 10 and 12). An advantage is the underside of collar 13 will be a smooth continuous surface (no clips protruding below the glass finger grip) which is important in the fluid filling line where the syringes are guided and located through processing by the underside of finger grips 139A, 139B.

Figure 15:
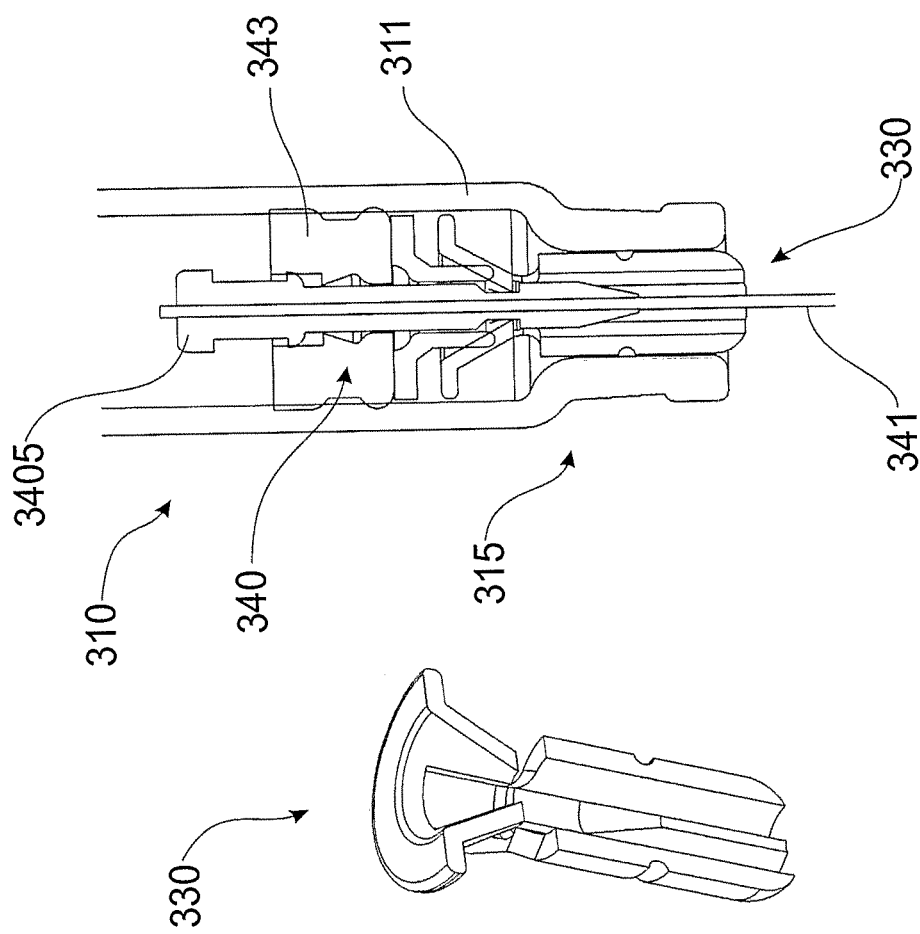
FIG. 15 provides perspective and sectional views of an alternative embodiment of a retaining member of a releasable needle retaining system.
Figure 15:
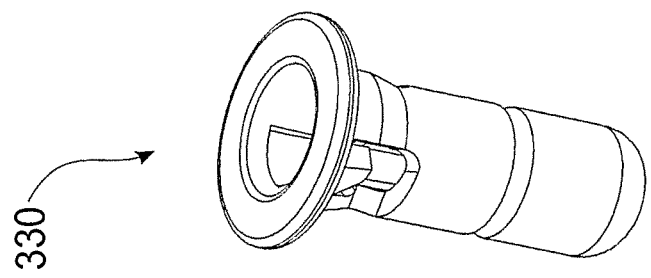
Figure 16:
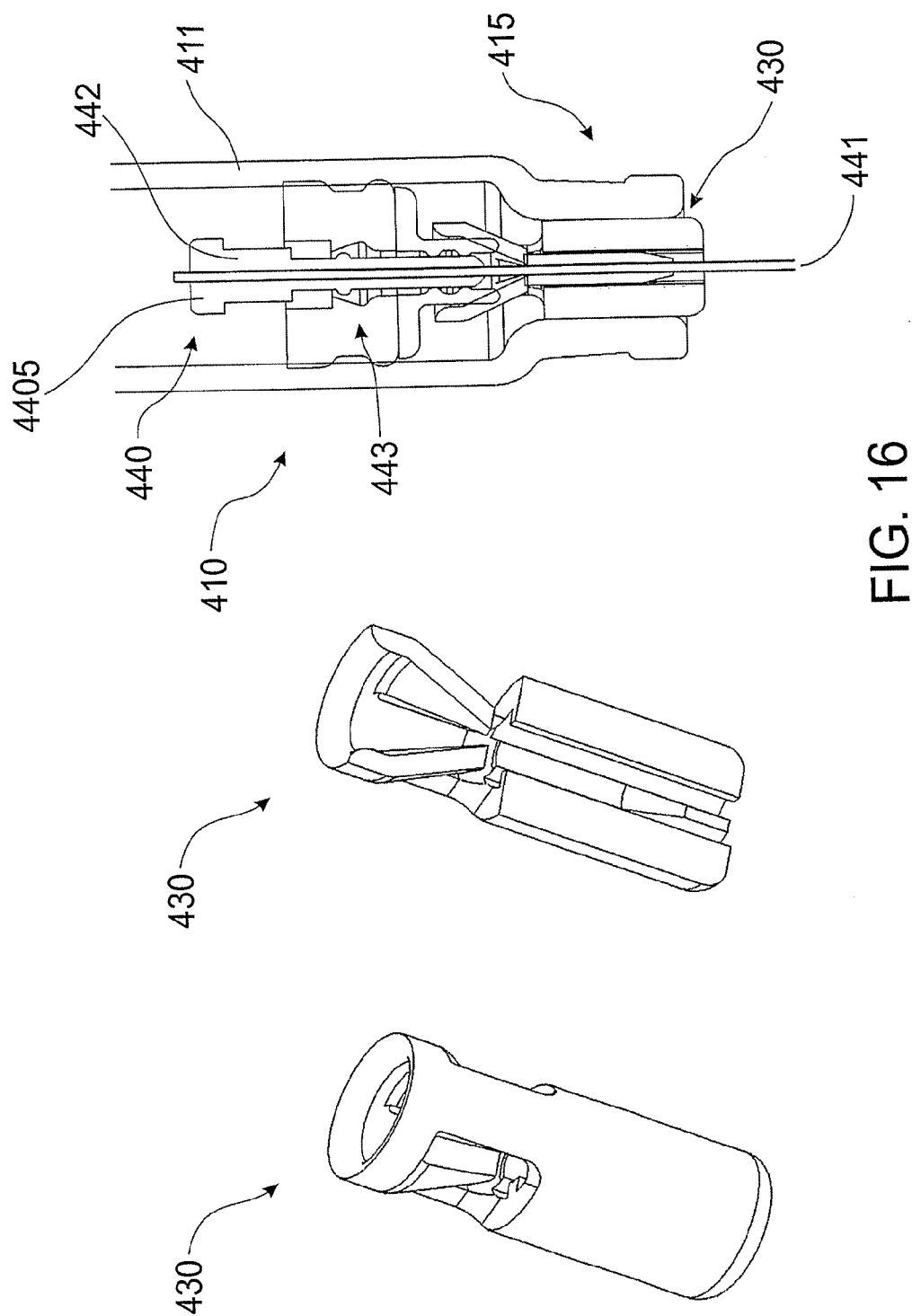
FIG. 16 provides perspective and sectional views of another alternative embodiment of a retaining member of a releasable needle retaining system.

Alternative embodiments of retaining member 30 are shown in FIGS. 15 and 16, although these require more complicated tooling (sliders) the designs do provide a saving in overall length. FIG. 15, shows needle retaining member 330 which is self locking and assembled at needle end 315 of syringe 310. This may provide a potentially stronger resistance to inadvertently pushing retractable needle 340 into barrel 311 during injection. FIG. 16 shows another smaller retaining member 430 which is self locking but assembled distally to needle end 415 of syringe 410.

Figure 17:
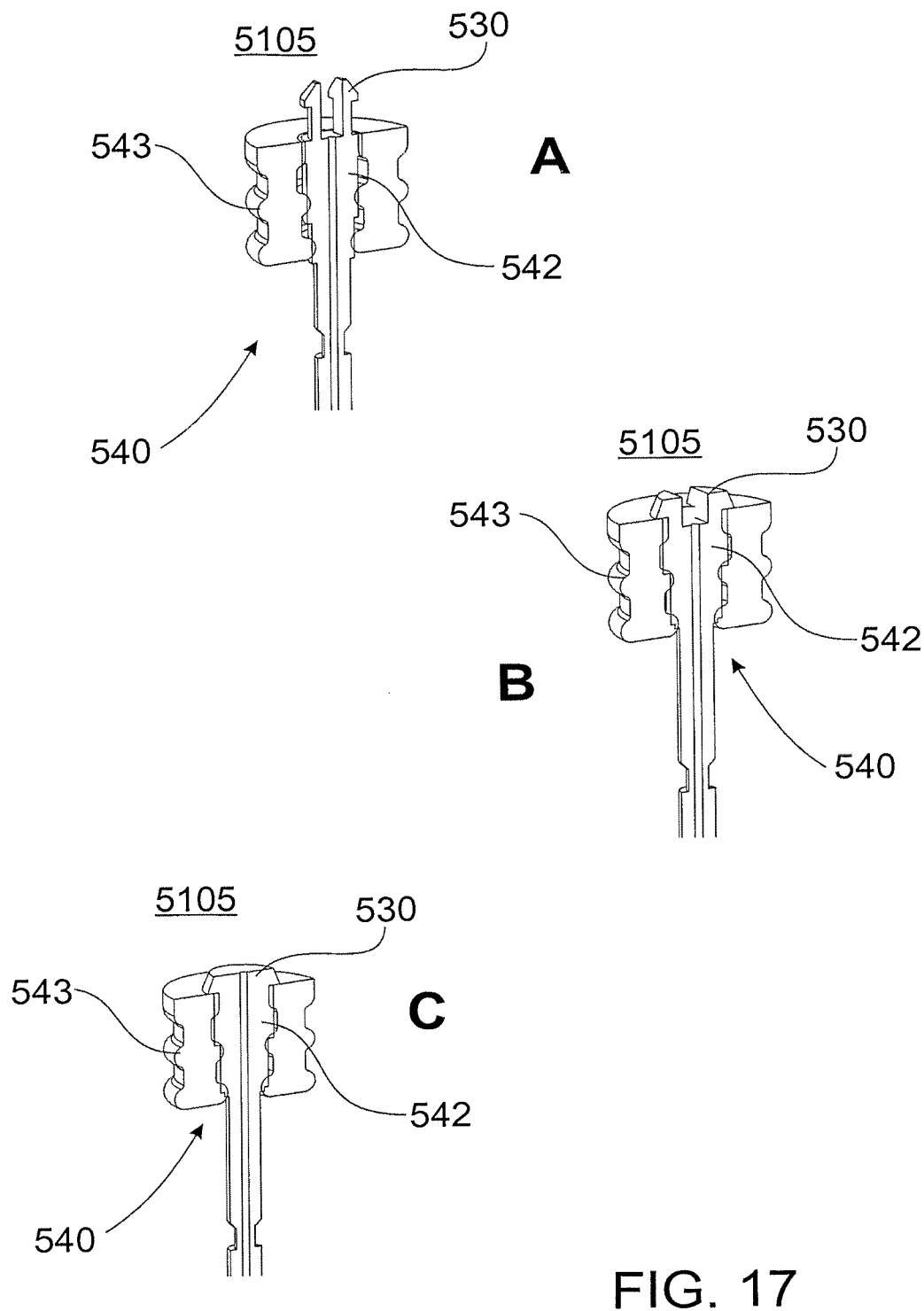
FIGS. 17A-C show alternative embodiments of a retractable needle engaged with a needle seal of a releasable needle retaining system.

Releasable needle retaining system 90 may also be varied. For example, retractable needle 40, particularly retractable needle body 42, may be varied as shown in FIGS. 17A, B & C where base 530 of retractable needle body 542 protrudes through needle seal 543 into the barrel fluid space 5105. This may stagger system forces and/or reduce overall plunger travel and/or provide a reduced force for plunger seal (not shown) to engage retractable needle body 542 as previously described.

Figure 18:
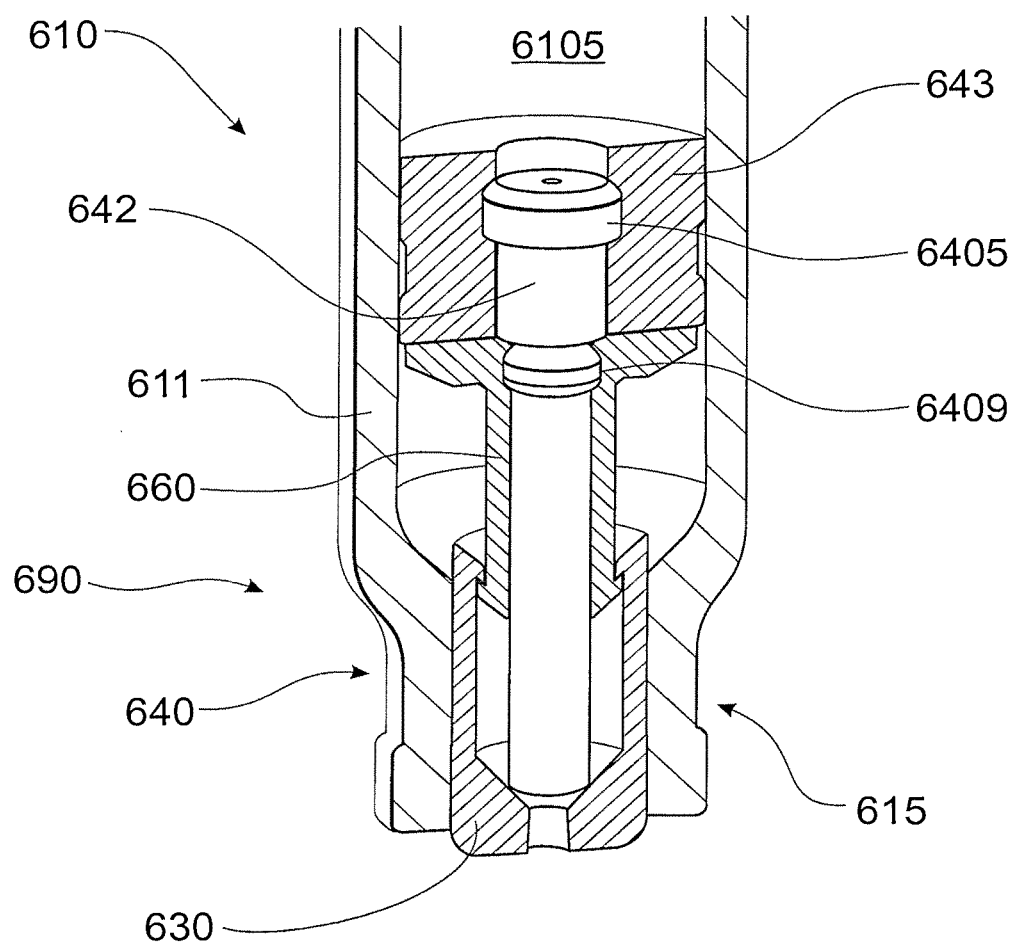
FIG. 18 shows another alternative embodiment of a releasable needle retaining system.

In another embodiment shown in FIG. 18, at needle end 615 of barrel 611 releasable needle retaining system 690 comprises needle seal 643 and ejector member 660 which holds retractable needle body 642 in place and retaining member 630 which serves to hold the retractable needle body 642 from moving forward. On retraction, ejector member 660 is pushed off detent 6409 around retractable needle body 642 allowing it to be free to be retracted (rather than opening fingers 31A, 31B, 31C on retaining member 30 as previously described) to allow retraction of needle 640. This eliminates the need for any radial orientation during assembly, is not affected by variations in internal glass barrel geometry and also reduces length, which assists ease of manufacture.

Figure 19:
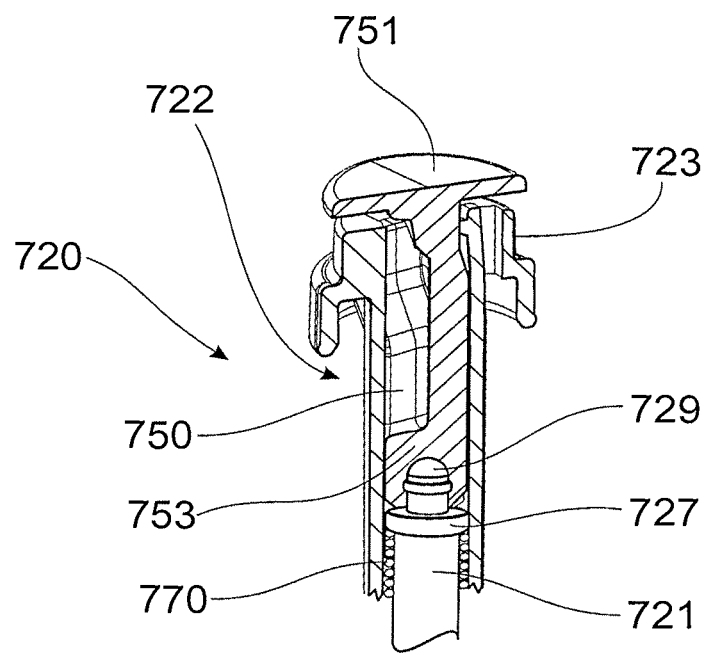
FIG. 19 shows perspective and sectional views of an alternative embodiment of a controlling member and a plunger rod.
Figure 19:
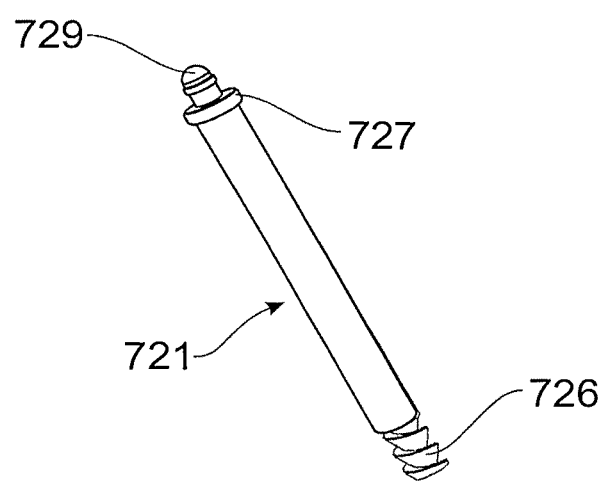

In another alternative embodiment of plunger 720, shaft 753 may comprise a connector that releasably engages a recess in plunger rod 721, while otherwise being arranged as described in FIGS. 2 and 3. An example is shown in FIG. 19, where controlling member 750 comprises a recess (not shown) which receives snap ring connector 729 on plunger rod 721.

In light of the aforementioned description of preferred embodiments of retractable syringe 10, a preferred mode of assembly of a prefilled retractable syringe 10 is as follows. Retaining member 30 and collar 13 are both glued to barrel 11 which is then siliconised. Retractable needle 40, ejector member 60 and needle seal 43 of releasable needle retaining assembly 90 are fitted into needle end 15 of barrel 11. These three components are held together as an assembly by head 405 of retractable needle 40 being retained by needle seal 43 and ejector member 60 engaging circumferential recess 420 on retractable needle body 42 via annular detent 63. Retractable needle body 42 also clips into fingers 31A-C of retaining member 30. Protective cover 12 is then fitted to barrel 11 at needle end 15. Barrel 11 is then filled with fluid contents and plunger seal 80 is subsequently inserted inside barrel 11 to a position adjacent the fluid contents without pressurising the fluid contents. Typically, a nitrogen gas gap is located between the fluid contents and plunger seal 80. The fitting of plunger seal 80 thereby provides a sterile container for the fluid contents. Plunger outer 22, plunger rod 21 with controlling member 50 and spring 70 are pre-assembled into a plunger 20 assembly which is subsequently screw-fitted into plunger seal 80.

Components of retractable syringe 10 have been designed to provide ease of manufacture to the extent that plastic components require only open-shut tooling (e.g. no sliders are required) which not only makes tooling less expensive and less complicated, but open/shut tools are much more reliable for high volume production.

Minimal orientation is required for assembly of retractable syringe 10. Only two components require orientation to fit together (controlling member 50 to plunger outer 22), but they are easily oriented in the automated assembly process, and the orientation is justified by functional advantages.

Design of retractable syringe 10 considers the broader manufacturing tolerances of glass barrels (compared to plastic moulding tolerances) which have a length tolerance of +/−0.5 mm. To overcome the broad length tolerance retractable syringe 10 has been designed to allow the retaining member 30 to be glued into position at needle end 15 of barrel 11 with reference to collar 13 at plunger end 14 of barrel 11 to a tolerance of ±0.05 mm. This reduces the tolerance effect of the glass barrel 11 to provide a tighter activation of the retractable needle 40 retraction mechanism that is activated by release ring 136 triggering spring 70 release whilst retractable needle 40 is being released from retaining member 30.

Furthermore, ejector member 60 simply sits on needle seal 43 and also engages retractable needle body 42 via annular detent 63, which effectively locks the assembly of needle seal 43, ejector member 60 and retractable needle 40 together for assembly into glass barrel 11 as a unit. Retaining member 30 will already have been glued into place (at a set distance from collar 13) for location of retractable needle 40 as the assembly is moved into position in barrel 11.

For ease of assembly, plunger 20 as hereinbefore described comprises plunger rod 21 and controlling member 50 as a single part, with controlling member 50 being snapped off at frangible junction 24 after retraction. This reduces the number of components and eliminates connection detail between these two components.

In light of the foregoing it will be appreciated that the present invention provides a relatively simple, robust and inexpensive syringe that is automatically disabled with little or no assistance from the user to thereby prevent, or at least minimize the likelihood of, re-use of the syringe and/or needlestick injury by a used syringe.

Furthermore, by controlling or regulating the rate of needle retraction, the likelihood of blood splattering is reduced thereby improving the "user-friendliness" and commercial appeal of the retractable syringe.

The retractable syringe components are all designed to ensure the uniquely correct timing and efficient delivery of fluid contents, plunger engagement with the retractable needle and needle retraction as a particular feature of the syringe as herein described. Depression of the plunger rod "squeezes" the plunger seal lengthways against the needle seal which bears against the ejector member to ensure the ejector member has sufficiently spread the fingers of the retaining member to allow the retractable needle to be free to retract, but not before the last of the fluid contents have been delivered and the retractable needle securely engaged.

As previously described, manufacture and assembly of the retractable syringe is facilitated by the components described herein. In the context of a prefilled syringe, sterility is readily maintained and a retractable syringe sub-assembly (comprising a barrel fitted with a releasable needle retaining system together with a plunger and a separate plunger seal) can be provided for subsequent filling with fluid contents and completion of assembly.

Throughout the specification, the aim has been to describe the preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

The invention claimed is:

1. A releasable needle retaining system mountable to a syringe barrel, comprising:
    a retractable needle that comprises a needle body having a base and a cannula;
    a needle seal that seals against the inside wall of the barrel and releasably engages the base of the retractable needle prior to retraction; and
    a retaining member that comprises a cylindrical body comprising a mating surface complementary to a mating surface of an interior wall of said barrel, said retaining member comprising fingers that, in use, project proximally with respect to a user and are capable of initially retaining said retractable needle at a needle end of said barrel until said base of said retractable needle is engaged by a plunger to facilitate retraction of said retractable needle.

2. The releasable needle retaining system of claim 1, wherein the retaining member further comprises bosses that prevent movement of the retractable needle out of the syringe barrel.

3. The releasable needle retaining system of claim 1 which is mountable to a glass barrel.

4. The releasable needle retaining system of claim 1, further comprising an ejector member which facilitates release of the retractable needle from the retaining member.

5. The releasable needle retaining system of claim 4, wherein the ejector member releasably engages the retractable needle until prior to retraction of the retractable needle.

6. The releasable needle retaining system of claim 5, wherein the ejector member is capable of deforming the fingers of the retaining member to facilitate preventing re-use of the syringe after release of the retractable needle from the retaining member.

7. The releasable needle retaining system of claim 4, wherein the retaining member comprises deformable fingers which releasably engage said retractable needle and the ejector member is capable of displacing the fingers out of engagement with the retractable needle to thereby allow retraction of the retractable needle when engaged by the plunger.

8. The releasable needle retaining system of claim 4, wherein the ejector member bears against, or is unitary with, the needle seal.

9. The releasable needle retaining system of claim 1, wherein the needle body and the cannula are co-moulded.

10. The releasable needle retaining system of claim 1, wherein the mating surface of the cylindrical body of the retaining member can seal against the complementary mating surface of the interior wall of said barrel.

11. A retractable syringe comprising a barrel, a plunger, and a releasable needle retaining system comprising:
    a retractable needle that comprises a needle body having a base and a cannula;
    a needle seal that seals against the inside wall of the barrel and releasably engages the base of the retractable needle prior to retraction; and
    a retaining member that comprises a cylindrical body comprising a mating surface complementary to a mating surface of an interior wall of said barrel, said retaining member comprising fingers that, in use, project proximally with respect to a user and are capable of initially retaining said retractable needle at a needle end of said barrel until said base of said retractable needle is engaged by a plunger to facilitate retraction of said retractable needle.

12. The retractable syringe of claim 11, wherein the plunger comprises a plunger rod, a plunger outer, a controlling member for controlling the rate of needle retraction and a biasing member, wherein the plunger rod, plunger outer and the controlling member co-operate to releasably maintain said biasing member in an initially energized state.

13. The retractable syringe of claim 12, wherein the plunger rod comprises a seal capable of engaging the base of said retractable needle.

14. The retractable syringe of claim 12, wherein, said controlling member comprises one or more mating portions that initially engage said plunger outer to facilitate maintaining said biasing member in an initially energized state.

15. The retractable syringe of claim 12, wherein the controlling member and the plunger outer are releasably connected, whereby disengagement of the controlling member and the plunger housing facilitate release of said biasing member from said initially energized state.

16. The retractable syringe of claim 12, wherein the plunger rod and controlling member are releasably connected.

17. The retractable syringe of claim 12, further comprising one or more locking systems respectively comprising (i) elements of the plunger outer and the plunger rod; and/or (ii) elements of a collar mounted to the barrel and the plunger outer.

18. The retractable syringe of claim 11, wherein the barrel is a glass barrel.

19. A prefilled retractable syringe comprising:
    a glass barrel that comprises an interior wall and a collar having a releasing ring;
    a releasable needle retaining system comprising:
        a retractable needle that comprises a needle body having a base;
        a needle seal that seals against the inside wall of the barrel and releasably engages the base of the retractable needle prior to retraction; and
        a retaining member that comprises a cylindrical body comprising a mating surface complementary to a mating surface of an interior wall of said barrel, said retaining member comprising fingers that, in use, project proximally with respect to a user and are capable of initially retaining said retractable needle at a needle end of said barrel until said base of said retractable needle is engaged by a plunger to facilitate retraction of said retractable needle;
    a plunger engageable with the base of said retractable needle to facilitate retraction of the retractable needle; and
    one or more plunger locking systems.

20. The prefilled retractable syringe of claim 19, wherein the plunger comprises a plunger outer and a plunger rod, a plunger locking system formed between elements of the plunger outer and the collar.

21. The prefilled retractable syringe of claim 19, wherein the plunger comprises a plunger outer and a plunger rod, a plunger locking system formed between elements of said plunger rod and said plunger outer.

22. The prefilled retractable syringe of claim 19, wherein the mating surface of the cylindrical body of the retaining member seals against the complementary mating surface of the interior wall of said barrel.

* * * * *